US010398327B2

(12) United States Patent
Estepp et al.

(10) Patent No.: US 10,398,327 B2
(45) Date of Patent: Sep. 3, 2019

(54) NON-CONTACT ASSESSMENT OF CARDIOVASCULAR FUNCTION USING A MULTI-CAMERA ARRAY

(71) Applicant: Government of the United States, as represented by the Secretary of the Air Force, Wright-Patterson AFB, OH (US)

(72) Inventors: Justin R. Estepp, Centerville, OH (US); Ethan B. Blackford, Beavercreek, OH (US); Christopher M. Meier, Greenville, OH (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 0 days.

(21) Appl. No.: 16/131,080

(22) Filed: Sep. 14, 2018

(65) Prior Publication Data
US 2019/0008402 A1   Jan. 10, 2019

Related U.S. Application Data

(62) Division of application No. 14/870,148, filed on Sep. 30, 2015, now abandoned.

(60) Provisional application No. 62/059,870, filed on Oct. 4, 2014.

(51) Int. Cl.
| | |
|---|---|
| *A61B 5/024* | (2006.01) |
| *G06K 9/46* | (2006.01) |
| *A61B 5/00* | (2006.01) |

(52) U.S. Cl.
CPC ........ *A61B 5/02416* (2013.01); *A61B 5/0075* (2013.01); *A61B 5/6887* (2013.01); *A61B 5/7214* (2013.01); *A61B 5/7235* (2013.01); *G06K 9/46* (2013.01); *A61B 5/02433* (2013.01)

(58) Field of Classification Search
CPC .... G06K 9/46; A61B 5/0075; A61B 5/02416; A61B 5/02433; A61B 5/6887; A61B 5/0077; A61B 5/7235; A61B 5/7214
USPC ........................................................ 600/479
See application file for complete search history.

(56) References Cited

U.S. PATENT DOCUMENTS

| | | | |
|---|---|---|---|
| 2007/0265533 A1* | 11/2007 | Tran ........................ | A61B 5/021 600/481 |
| 2013/0322729 A1* | 12/2013 | Mestha .................... | A61B 5/02 382/134 |
| 2014/0323888 A1* | 10/2014 | Kyal ................... | A61B 5/02405 600/508 |

\* cited by examiner

*Primary Examiner* — Eric D. Bertram
*Assistant Examiner* — Pamela M. Bays
(74) *Attorney, Agent, or Firm* — AFMCLO/JAZ; Charles Figer, Jr.

(57) ABSTRACT

A method is provided for non-contact cardiac assessment of a subject. Images of the subject are captured from at least two synchronized independent imaging devices spaced equidistant from the subject and positioned such that each imaging device captures an image of the subject different from other imaging devices. Spectral components of the captured images are extracted. The extracted spectral components are analyzed. A signal corresponding to cardiac information is identified in the extracted spectral components. The identified signal corresponding to the cardiac information is extracted from the extracted spectral components.

7 Claims, 8 Drawing Sheets

NON-CONTACT ASSESSMENT OF CARDIOVASCULAR FUNCTION USING A MULTI-CAMERA ARRAY

CROSS-REFERENCE TO RELATED APPLICATIONS

This application is a divisional of U.S. application Ser. No. 14/870,148, entitled "Non-Contact Assessment of Cardiovascular Function using a Multi-Camera Array," filed on Sep. 30, 2015, which claims the benefit of and priority to U.S. Provisional Application Ser. No. 62/059,870, entitled "Multi-Camera Array for Noncontact Assessment of Cardiovascular Function," filed on Oct. 4, 2014, the entireties of which is incorporated by reference herein.

RIGHTS OF THE GOVERNMENT

The invention described herein may be manufactured and used by or for the Government of the United States for all governmental purposes without the payment of any royalty.

BACKGROUND OF THE INVENTION

Field of the Invention

The present invention generally relates to non-contact sensing of physiological functions and, more particularly, non-contact sensing of cardiovascular functions.

Description of the Related Art

Cardiac monitoring has been sufficiently demonstrated as a method for assessing wellness, performance, cognitive, and stress states in everyday, clinical, and mission environments. This monitoring is traditionally derived from one of two different modalities: electrocardiography (ECG) or photoplethysmography (PPG).

Electrocardiography measures electrical potentials produced by the depolarization and repolarization of the various muscles of the heart as they pump blood to the body. These electrical potentials propagate to the skin's surface where they may be measured using surface electrodes. Measures of cardiac activity derived from ECG have been demonstrated, in numerous studies, to be sensitive to physiological changes related to the demands of piloting aircraft. Cardiac measures of both heart rate and heart rate variability have also been shown to be sensitive to flight maneuvers and segments in an operational tactical airlift aircraft. These contemporary results were utilized to aid in a decision making process related to changes made to the cockpit systems in the aforementioned platforms. Additional studies focused on workload evaluation in current operational missions, a large portion of which are similar to the approach used in the tactical airlift aircraft study as related to the assessment of cardiac activity for objective measurement of stress and workload. ECG is often considered the "gold standard" for measuring cardiac activity in both clinical and research areas because it directly measures the aggregate electrical activity produced by the muscles pumping blood in the heart. Unfortunately, ECG requires electrodes to be affixed to the skin surface, costing time and resources, as well as a potential discomfort to the subject. It also may not be suitable for long term/repeated monitoring or with individuals with high skin sensitivities. Additionally, ECG may be susceptible to artifact under conditions of motion, which shake the ECG leads or disturb the electrode-skin interface. Moreover, these problems are also present in more modern "wearable" sensors that are popular in fitness, mobile health and wellness, and consumer electronics arenas.

Another monitoring methodology for observing cardiovascular performance is plethysmography. Plethysmography is a measurement of blood flow, or more specifically blood volume, in the peripheral vasculature. Contact photoplethysmography (PPG) is most common and utilizes (non-specific) light-based sources as a transduction medium. PPG takes advantage of well-known absorbent and reflective properties of tissue and blood as they vary with wavelength(s) of the transducer. The most common application of PPG is in pulse oximetry devices, which are usually secured to a finger, toe, or earlobe. Such devices measure arterial oxygen saturation and may also be capable of measuring pulse rate and pulse rate variability (which are often employed as surrogates of heart rate and heart rate variability). Unfortunately, traditional PPG sensors require a mounted sensor which may obstruct physical activity or may be uncomfortable for prolonged monitoring. Furthermore, contact PPG sensors experience a high degree of motion sensitivity which may corrupt the collected signal when the sensor-skin interface is disturbed.

PPG and, subsequently, pulse oximetry, are made possible due to a phenomenon known as an optical window where skin tissue exhibits relatively low absorption for visible and near-infrared light wavelengths between 400-2000 (nm). This property is primarily determined by the absorption spectra for water and skin pigments, particularly melanin. By contrast, blood and hemoglobin exhibit significantly higher absorption for wavelengths in the same region. As light enters the tissue, multiple complex interactions occur including absorption, reflection, scattering, transmission, and fluorescence, although absorption tends to be more important in the creation of an observed PPG signal. The total light absorption is a summation of a periodic AC signal associated with pulsatile blood volume changes and a low-frequency (to DC) offset component associated with absorption by the tissue, venous, and arterial blood. This AC signal component is created as heart contractions send pulsatile blood volumes to the peripheral vasculature that are observed as small, periodic changes in light absorption resulting from the varying blood volume in the underlying vasculature. The PPG signal may be measured in transmission mode, with the light source on the opposite side of the tissue as the sensor, or in reflection mode, where the light source and sensor are located on the same side of the tissue. Reflection mode is most common for imaging photoplethysmography (iPPG) applications where the photoplethysmogram is derived as a net intensity, over a region of interest, observed from reflected light that is captured by an imager.

Early work in the area of iPPG demonstrated pulsatile components with frequency characteristics (and their harmonics) similar to those of the photoplethysmogram (PPG) could be extracted from monochromatic imagery of a fingertip. This phenomenon was also observed in narrow-band wavelength imagery of a forearm at wavelengths of 660, 810, and 940 (nm), along with a lower frequency component related to respiration rate.

While monochromatic images composed of visible and NIR light or narrow-band wavelengths in the red and NIR range, undoubtedly inspired by traditional PPG and pulse oximetry methods were traditionally used, it was demonstrated that superficial arterial pathways in the neck (e.g., the carotid arteries) could be isolated in mid-wave infrared (MWIR) imagery, which also showed spectral peaks in a frequency-domain representation of the MWIR imagery data that were likely to be related to pulse rate. Near-infrared region bands were used despite very well documented evidence that oxyhemoglobin exhibits the most absorption for wavelengths in the green band, which is largely responsible for the pulsatile component of the PPG that links to cardiac cycle rhythms.

iPPG from facial imagery showed improved iPPG data quality by using red, green, and blue (RGB) channels from visible spectrum imagery as the channel input space to an independent component analysis (ICA) decomposition. This decomposition improved estimates of cardiac measures (as compared to fingertip PPG) beyond those achieved using only the green source channel (where the iPPG signal appears to be most prominent). By extracting inter-beat interval (IBI) time series from the iPPG component, strong correlations for features related to heart rate variability were shown as compared to fingertip PPG. Additional work focused on exploring practical issues of the methodology such as imager quality, frame rate requirements, facial ROI selection for improved channel space signal-to-noise ratio (SNR), and applied testing of iPPG in clinical environments.

However, one practical issue that has not yet been addressed is that of head motion artifact and its effect on pulse rate component recovery from the ICA (or other blind source separation approach) decomposition of the imager channel space. Contemporary methodologies either restrict head motion to a limited range or eliminate it completely from the design. With cardiac activity monitoring likely playing an important role in short-term operational evaluations and decision making processes, as well as long-term research in the areas of applied neuroscience and closed-loop decision aid systems, the potential user acceptance of a non-contact assessment methodology that is as good as, or better than, traditional contact methods in terms of data quality and robustness would be an invaluable step toward transitioning long-term, persistent physiological monitoring to day-to-day operations. Accordingly, there is a need in the art for improved PPG methodologies that are not as susceptible to artifacts from head or other movement of the subject.

SUMMARY OF THE INVENTION

Embodiments of the invention provide a method for non-contact cardiac assessment of a subject. Images of the subject are captured from at least two synchronized independent imaging devices. The imaging devices are spaced equidistant from the subject and are positioned such that each imaging device captures an image of the subject different from other imaging devices. Spectral components of the captured images are extracted. The extracted spectral components are analyzed. A signal corresponding to cardiac information is identified in the extracted spectral components. Finally, the signal corresponding to the cardiac information is extracted from the extracted spectral components. In some embodiments of the invention, capturing the images of the subject from at least two synchronized independent imaging devices includes capturing head and neck images of the subject from the at least two synchronized independent imaging devices.

In some embodiments, extracting spectral components of the captured images includes extracting Red, Green, and Blue components of the captured images. In some embodiments, analyzing the extracted spectral components includes performing an independent component analysis on the extracted spectral components. In other embodiments, identifying a signal in the extracted spectral components corresponding to cardiac information includes bandpass filtering the extracted spectral components between about 0.3 Hz and about 6 Hz. The extracted spectral components are upsampled to about 1200 Hz using cubic spline interpolation. A signal is chosen from the extracted spectral components based on an estimate of signal-to-noise ratio (SNR) in an expected frequency range of a non-contact PPG (ncPPG) component signal. In these embodiments, the expected frequency range of a ncPPG component signal may be about 0.75 Hz to about 4 Hz. In other embodiments, extracting the signal in the extracted spectral components corresponding to the cardiac information includes transforming band power estimate to relative power by dividing by component signal power outside a peak frequency range but within about 0.75 Hz top about 4 Hz. In these embodiments, an independent component is extracted with a highest relative power. Additionally in these embodiments, the extracted component may be segmented into five non-overlapping windows. A frequency may be found with a highest power density in a probable pulse rate range. This frequency may then be converted to beats per minute by $60 \cdot f_{max}$, where $f_{max}$ is the frequency with the highest power density.

Embodiments of the invention also provide a system for non-contact cardiac assessment of a subject. The system includes at least two imaging devices configured to individually capture images of the subject. The imaging devices are spaced equidistant from the subject and positioned such that each imaging device captures an image of the subject different from other imaging devices. A data acquisition card is in electrical communication with the at least two imaging devices. At least one computer is in electrical communication with the at least two imaging devices and configured to receive the captured images from the at least two imaging devices, extract spectral components of the captured images, analyze the extracted spectral components, identify a signal in the extracted spectral components corresponding to cardiac information, and extract the signal in the extracted spectral components corresponding to the cardiac information. Trigger signals generated by the data acquisition card cause images to be captured simultaneously by the imaging devices and delivered to the computer.

In some embodiments, the subject is positioned at a distance of about 68 inches from the imaging devices. Alternate configurations of the imaging devices may include three imaging devices positioned about 20 degrees apart, spanning about 40 degrees of visibility of the subject, five imaging devices positioned about 30 degrees apart, spanning about 120 degrees of visibility of the subject, nine imaging devices positioned about 20 degrees apart, spanning about 160 degrees of visibility of the subject, four imaging devices positioned about 40 degrees apart, spanning about 120 degrees of visibility of the subject, among others. In some embodiments, the imaging devices are positioned at a height to capture head and neck images of the subject. The arrangement of the imaging devices in some embodiments are positioned along a semi-circle. Some embodiments of the invention also include at least two lights sources, each light source corresponding to one of the imaging devices, where the light sources are mounted above the at least two imaging devices. In these embodiments, the two light sources may be mounted approximately 18 inches above the imaging devices.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

Photoplethysmography (PPG) relies on characteristic changes in the optical absorption of tissue due to pulsatile (arterial) blood flow in peripheral vasculature. Sensors for observing the photoplethysmographic effect have traditionally required contact with the skin surface. Recent advances in non-contact imaging PPG have demonstrated that measures of cardiopulmonary system state, such as pulse rate, pulse rate variability, and respiration rate, can be obtained from a participant by imaging their face under relatively motionless conditions. A critical limitation in this method that must be resolved is the inability to recover these measures under conditions of head motion artifact.

Embodiments of the invention address the need in the art by utilizing multiple synchronized, visible spectrum imagers positioned in an array centered on an imaged participant. Increased measurement error during motion artifact is mitigated by the embodiments of the invention by the increased dimensionality of the imager channel space with multiple imagers in the array prior to applying a blind source separation. In contrast to single-imager results, the multi-imager channel space results in an absolute error in the recovered pulse rate measurement that is comparable with pulse rate measured via fingertip reflectance photoplethysmography. These results demonstrate that non-contact, imaging photoplethysmography can be accurate in the presence of head motion artifact when utilizing embodiments of the invention implementing a multi-imager array to increase the dimensionality of the decomposed channel space.

Figure 1:
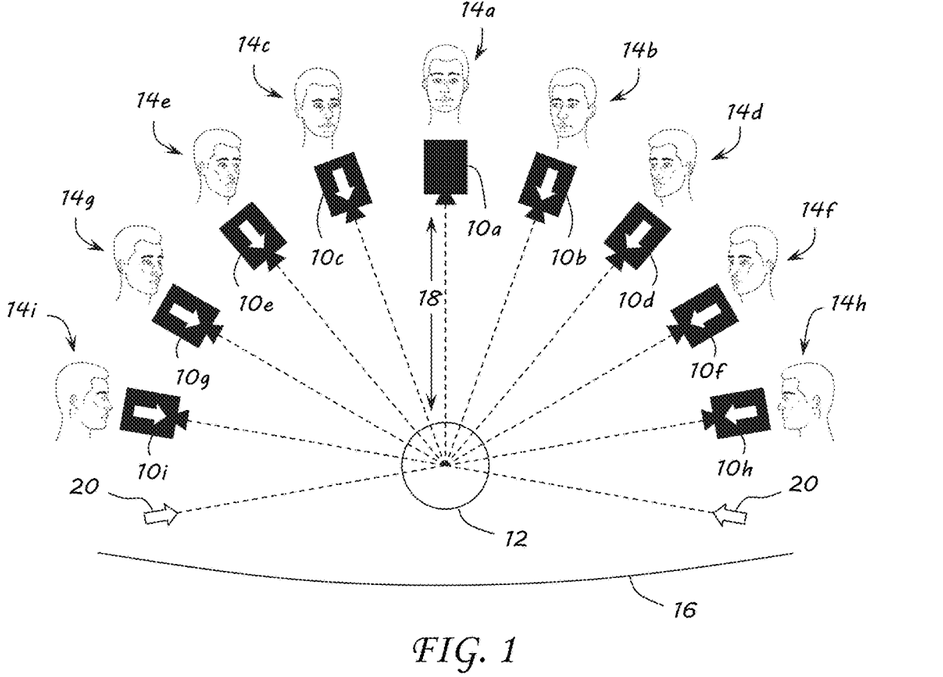
FIG. 1 is schematic diagram of a multi-camera arrangement for assessment of cardiovascular functions consistent with embodiments of the invention.

Embodiments of the invention replace traditional contact, cardiac monitoring with a synchronized array of digital video cameras collecting video data of an individual's face and neck. Turning now to the drawings, wherein like numbers denote like parts throughout the several views, FIG. 1 illustrates an exemplary embodiment including an array of nine synchronized digital video cameras 10a-i in a semi-circular arrangement around an individual 12 capturing simultaneous views 14a-i in front of an arbitrary background 16. Cardiac information results from an analysis and signal processing of small variations in reflected color information from an individual's 12 skin. This process is referred to as non-contact photoplethysymography (ncPPG). ncPPG relies on the same physical phenomena as traditional, contact PPG. The variations in reflected color intensity result from the fluctuating absorption and reflection of the blood volume pulsing through the peripheral vasculature of the skin throughout the cardiac cycle. In ncPPG, these variations are collected at a distance 18 from an imager 10a-i, instead of at the skin's surface with a sensor. Utilizing an array of imagers, such as cameras 10a-i, provides simultaneous views of the subject from multiple angles with continuous coverage of the face, even during movement. This allows the fluctuating PPG component to be continuously recorded, despite the orientation or movement of the individual 12 in frame. The improved and continuous views of the individual 12 provide more and higher quality inputs into a signal processing pipeline (see FIG. 6) (specifically a blind source separation component) allowing for a robust collection of cardiac information during movement. Embodiments of the invention show great improvements from single imager setups documented elsewhere which are highly susceptible to motion artifacts.

Figure 2:
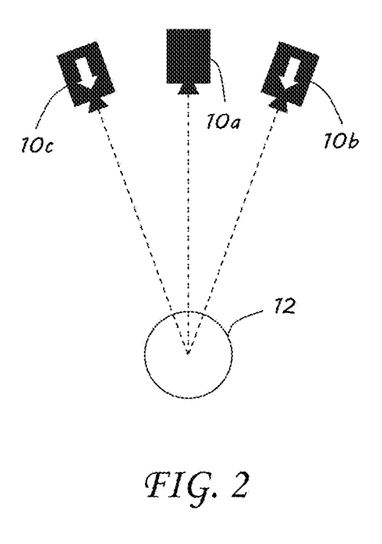
FIG. 2 is an alternate embodiment of the multi-camera arrangement of FIG. 1.
Figure 3:
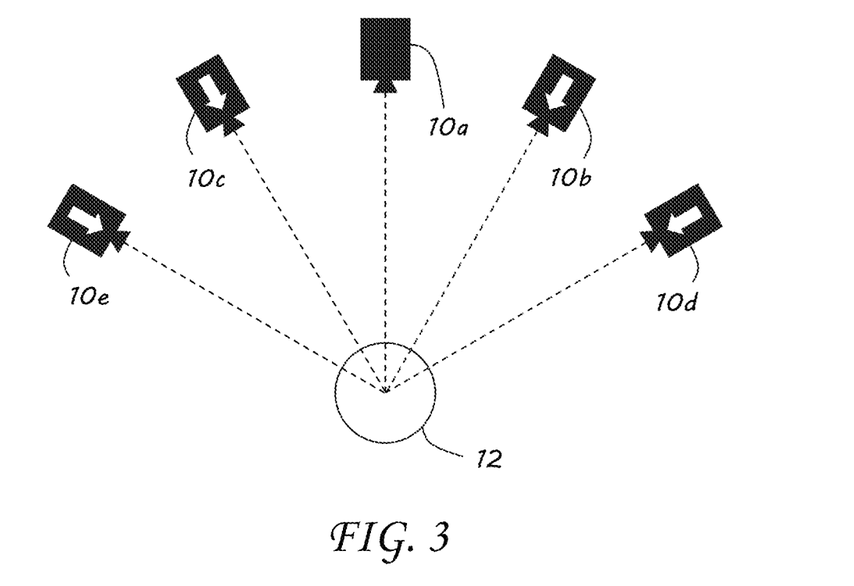
FIG. 3 is another alternate embodiment of the multi-camera arrangement of FIG. 1.
Figure 4:
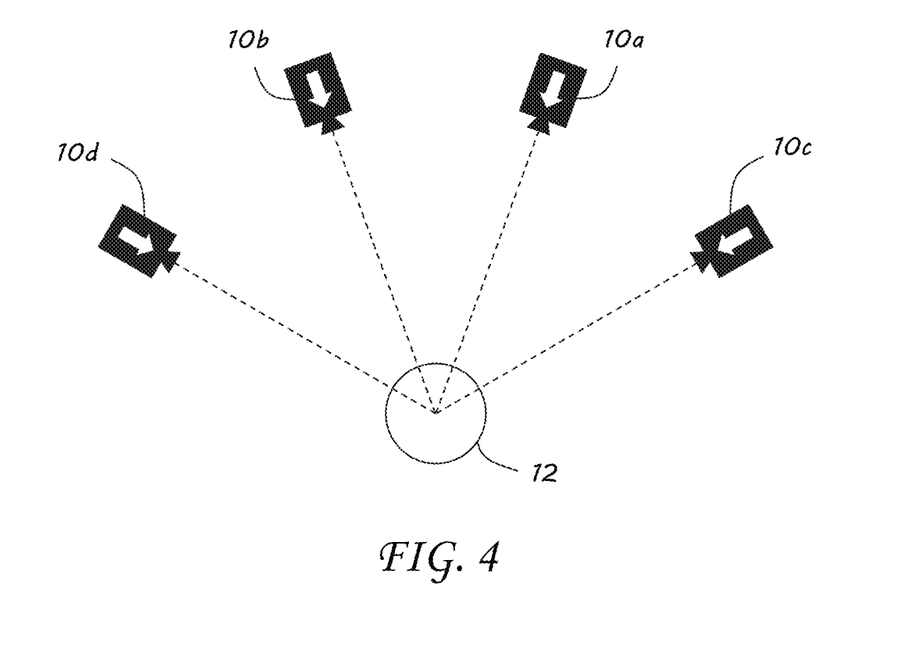
FIG. 4 is still another alternate embodiment of the multi-camera arrangement of FIG. 1.

In the exemplary embodiment illustrated in FIG. 1, the nine imager 10a-i semi-circular array consists of Basler Scout acA640-120gc GigE standard color progressive scan cameras with global shutter, capable of rendering 12-bit RGB pixel depth images at VGA resolution (640×480 pixels) at 120 frames per second (fps), though other comparable cameras from other manufacturers may also be utilized. Each imager is equipped with a 16 [mm] fixed focal length lens to maximize an area in each frame occupied by the individual's 12 face. In this illustrated embodiment, each camera 10a-i is supported by a tripod and positioned to align the camera 10a-i with the level of the individual's 12 face. Other embodiments may utilize other methods of placing cameras around the individual 12 by, for example, fixing the cameras to the surrounding environment or by suspending the cameras. The cameras 10a-i are spaced to occupy approximately a 160° semi-circle centered on the individual 12 with about 20° between each camera 10a-i. The total range of the array, ±80° from normal was chosen based on a maximum normal head rotation range of an individual 12, though other ranges, separations, and number of cameras may also be used. For example, as illustrated in FIG. 2, a three camera set up covering 40 degrees is illustrated. Much of the quality input may be collected from the center cameras, especially when movement of the individual 12 may be limited. In FIG. 3, a five camera setup covering 120 degrees is illustrated. In this embodiment, the cameras are spaced 30 degrees apart. FIG. 4, illustrates a four camera setup also coving 120 degrees. In this illustrated embodiment, the cameras are spaced 40 degrees apart. One of skill in the art will realize that number of cameras and spacing thereof can have any number of configurations and that such configurations will likely be dictated by the environment of the individual 12, whose cardiac information is being monitored. Returning to FIG. 1, the cameras 10*a-i* are positioned at a distance 18 of 68 inches away from the individual 12. Again, this distance is somewhat arbitrary and distances used in other embodiments may be dictated by the types of cameras being used as well as the overall environment in which the cameras are positioned.

Lighting (not shown) for the camera 10*a-i* array is provided by 10 SoLux black-back, full color spectrum (5000K) bulbs with a 36° beam spread. These bulbs simulate natural daylight spectrum, with nearly constant output power from 480 to 1080 [nm]. This additional lighting may be included or omitted in other embodiments, again depending on the lighting of the environment in which the cameras are positioned. These particular light sources are mounted approximately 18 inches above eight of the imagers 10*b-i* (the exception being the middle imager 10*a* in the array) and perpendicular to the normal vector of the imager. Additional light sources 20 may be positioned beyond the most extreme cameras 10*h*, 10*i* at the −100° and +100° positions of the semi-circle to ensure more even lighting. Again this additional lighting may be included or omitted in other embodiments, again depending on the lighting of the environment in which the cameras are positioned.

Figure 5:
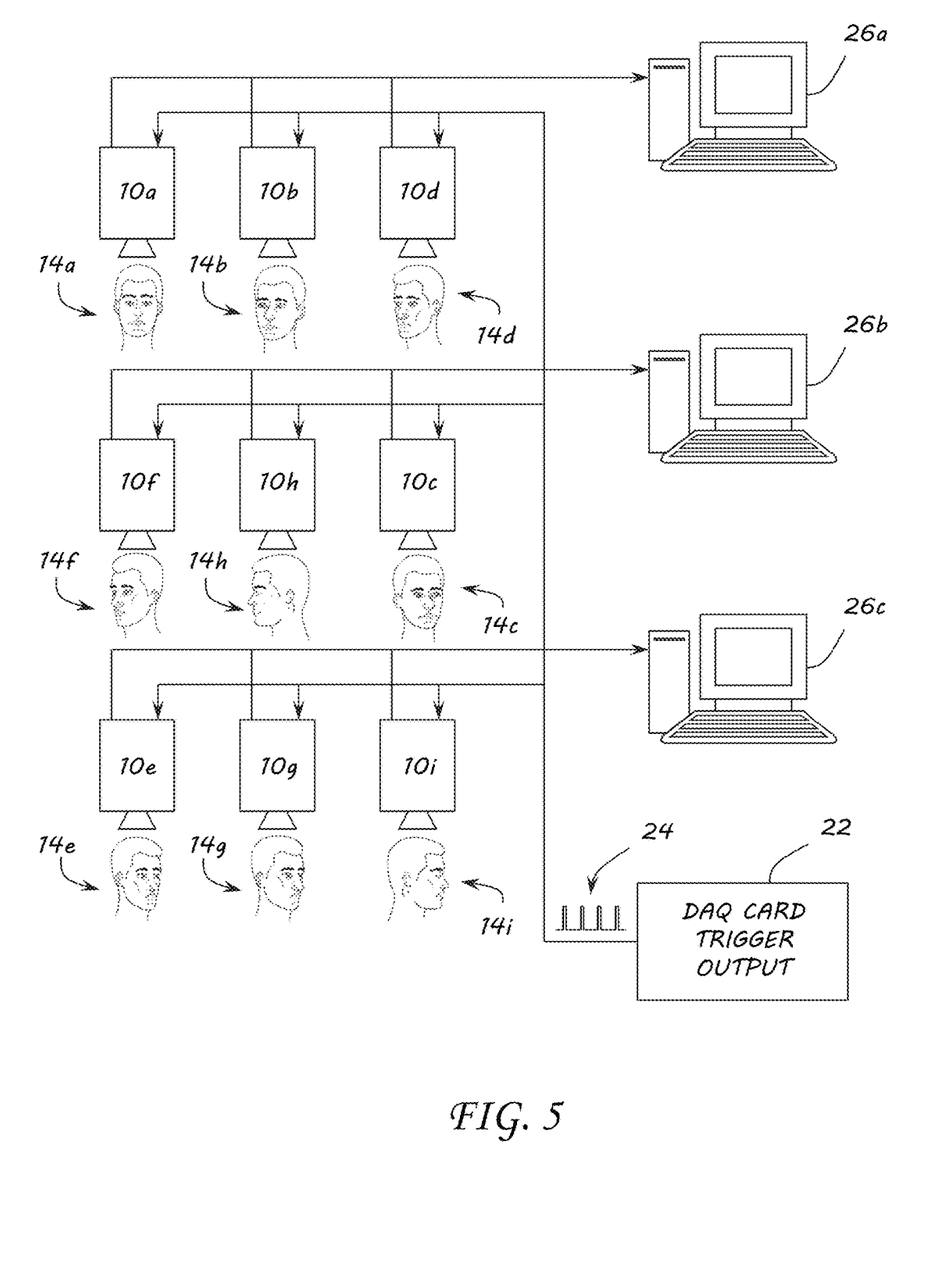
FIG. 5 is a schematic diagram of camera triggering and data flow from the multi-camera arrangements consistent with the embodiments in FIGS. 1 through 4.

Turning now to FIG. 5, the camera array 10*a-i* is synchronized with a National Instruments (NI) data acquisition card (DAQ) 22, model PCIe-6323, mounted in a workstation-class PC. Other embodiments of the invention may use other DAQ hardware or other sychnonizing schemes. The DAQ outputs a hardwire-timed pulse 24 train at 120 Hz and 90% duty cycle to the input controls of the nine imagers 10*a-i*. This ensures synchronous exposure and capture of the cameras across the array. While pulse train 24 is used in this illustrated embodiment, other embodiments of the invention may use other triggers to synchronize the outputs of the cameras 10*a-i*.

The imager data is collected using three NI quad port GigE video acquisition boards, model PCIe-8235, mounted in three separate workstation-class PCs 26*a-c*. Each PC 26*a-c* and three corresponding cameras form a pod whose raw, BG BAYER format data is recorded as a binary stream to a PCIe-mounted solid state hard drive. The pod configuration and solid state hard drives are used to support the data acquisition rate necessary for the simultaneous acquisition of imager array. While the illustrated embodiment utilizes the PC and camera pod configuration, other hardware configurations may also be used utilizing more or fewer computer or other electronic programmable devices, e.g., multi-user or single-user computers, desktop computers, portable computers and devices, handheld devices, network devices, mobile phones, etc. The number and of devices may be dictated based on the number of cameras capturing images or processing capability of the device.

Figure 6:
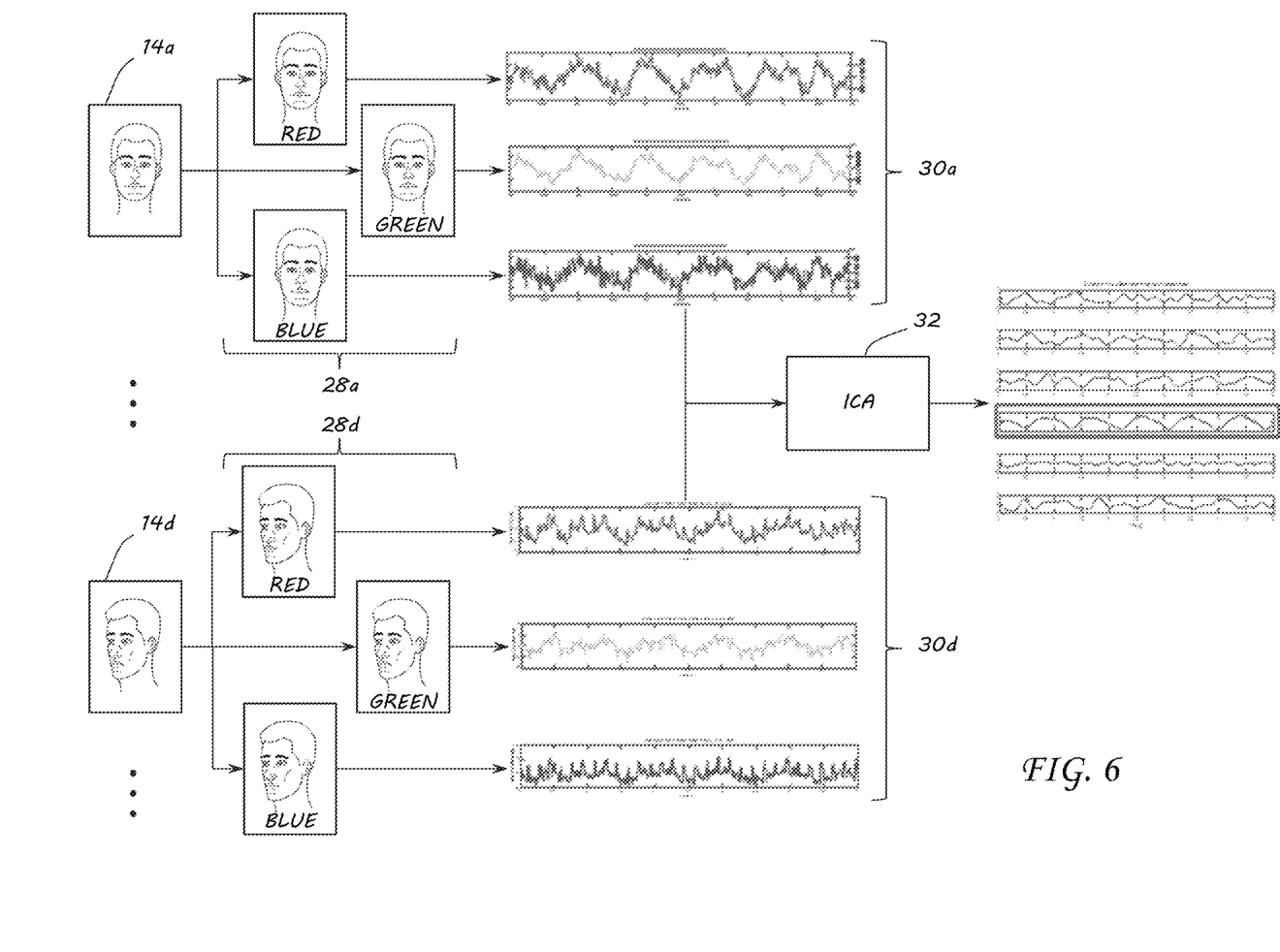
FIG. 6 is an exemplary flow diagram of a process pipeline consistent with schematic diagrams of FIGS. 1 through 5.

The stored raw, BG BAYER format binary data is recalled, though in other embodiments, instead of storing data for later recall, the processing of the data may be accomplished in real time. The raw data is demosaiced to form an RGB image, such as 28*a* and 28*d* as seen in FIG. 6. Mean/average RGB traces such as 30*a*, 30*d* are then calculated and recorded for the entire image frame. These mean RGB signals serve as the raw signal to extract the desired measures of cardiac activity. Other embodiments may choose different regions of interest from which to extract mean RGB traces. These embodiments may define the region of interest through face tracking, skin pixel detection, or other means, for example.

Figure 7:
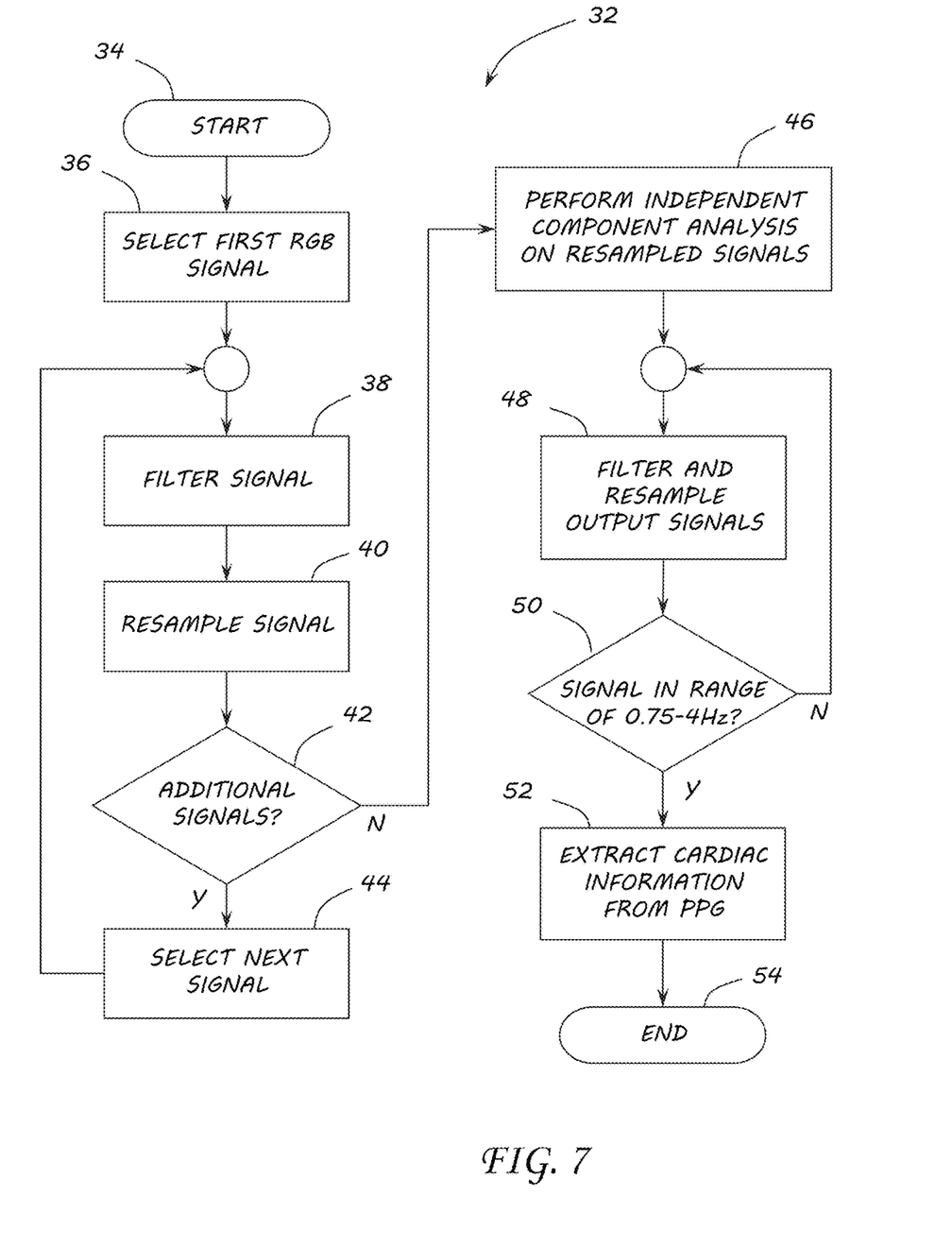
FIG. 7 is an exemplary flow diagram illustrating extraction of Cardiac information from the multi-camera arrangement of FIG. 1.

The mean RGB signals may be processed following contemporary processing routines, such as by Poh, McDuff, and Picard (2011). Notable exceptions to the contemporary signal processing routine are the use of 27 channels for ICA (9 cameras×RGB) vs. 3 channels (1 camera×RGB) and an automatic identification of the PPG component. Turning to flowchart 32 in FIG. 7, this process begins at block 34 and includes the following steps:

A first signal of the 27 mean RGB signals is selected in block 36. The signal is filtered with a band-pass filter between about 0.3 Hz and about 10 Hz in block 38 to eliminate any signal components that are outside a range of a typical cardiac signal. The filtered signal is then resampled from about 120 Hz to about 1,200 Hz using a spline interpolation to refined temporal resolution of the signal in block 40. Other embodiments may resample the signals using other frequencies and interpolations to improve temporal resolution. If there are additional signals ("Yes" branch of decision block 42), then the next signal is selected in block 44, and the filtering 38 and resampling 40 is repeated for this signal. If there are no additional signals, ("No" branch of decision block 42), then the filtered, resampled signals are input into an extended infomax, independent component analysis (ICA) algorithm in block 46. ICA is a type of blind source separation, which isolates independent components present in mixed data sources. This is accomplished through iterative maximization of non-gaussanity. From the algorithm, a number of underlying, independent components are output; one of which represents the PPG signal of interest while the others contain noise sources like movement. Other embodiments may use other types of analyses to isolate signal components.

After ICA, all independent components were bandpass filtered in block 48 with a zero-phase elliptical band pass filter between 0.3-6 (Hz) before upsampling the signal to 1200 (Hz) using cubic spline interpolation. As before, other filter and sampling of the signals may be used. The component most likely to contain PPG information is automatically chosen based on an estimate of signal-to-noise ratio (SNR) in the expected frequency range of the ncPPG component signal. In one particular embodiment, the method used a periodogram approach (with a Hamming window) to estimate the PSD of the components. Looking specifically at the frequencies and corresponding power densities from 0.75-4 (Hz) in block 50 (the likely pulse rate range corresponding to 45-240(bpm), the frequency with maximum power density is located and band power for that dominant frequency is calculated over a range of ±0.123 (Hz).

Figure 8A:
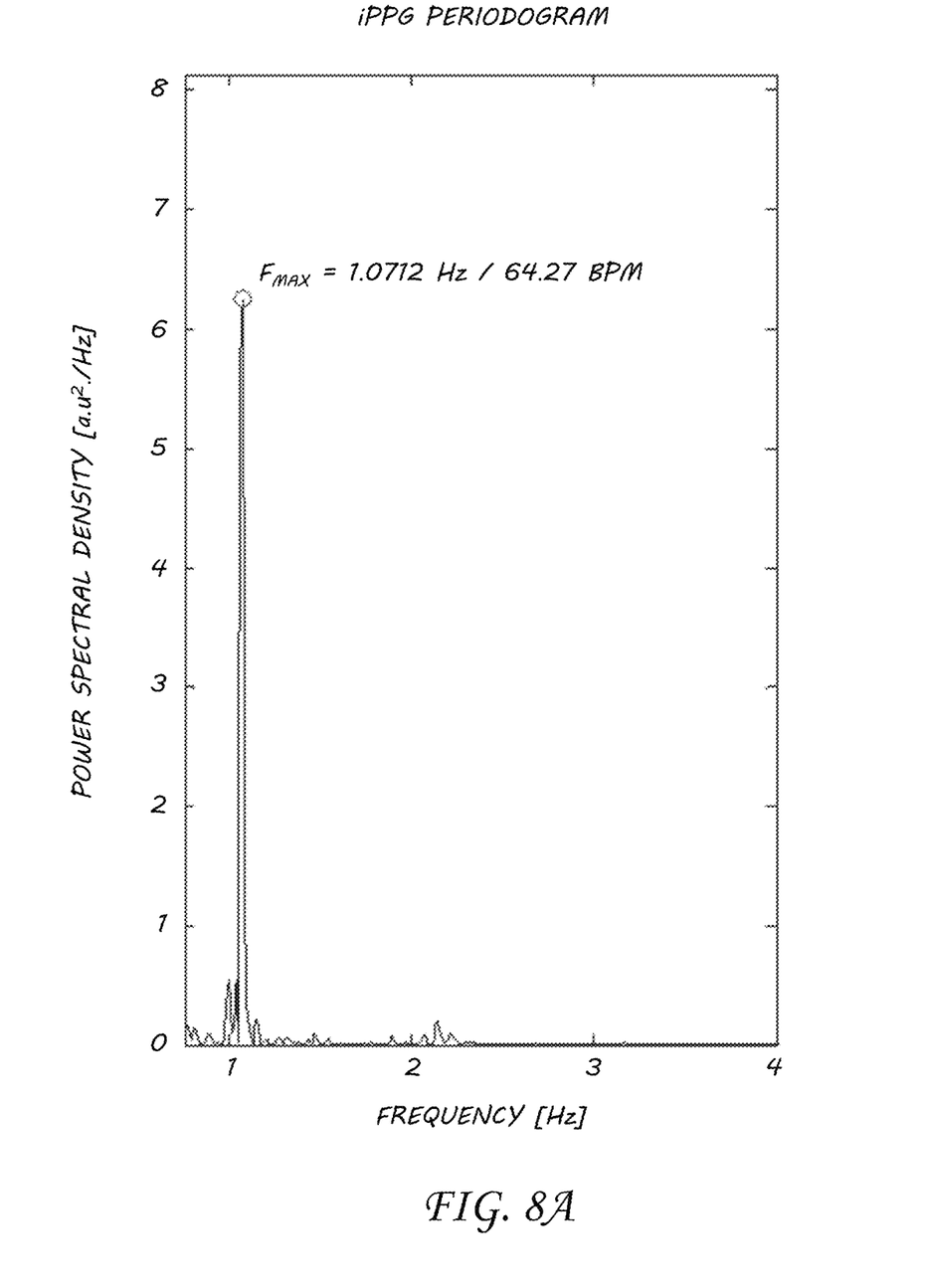
FIGS. 8A and 8B are graphs containing an exemplary periodogram for determining pulse rates from an automatically selected ncPPG component and an equivalent periodogram from a fingertip PPG time series.
Figure 8B:
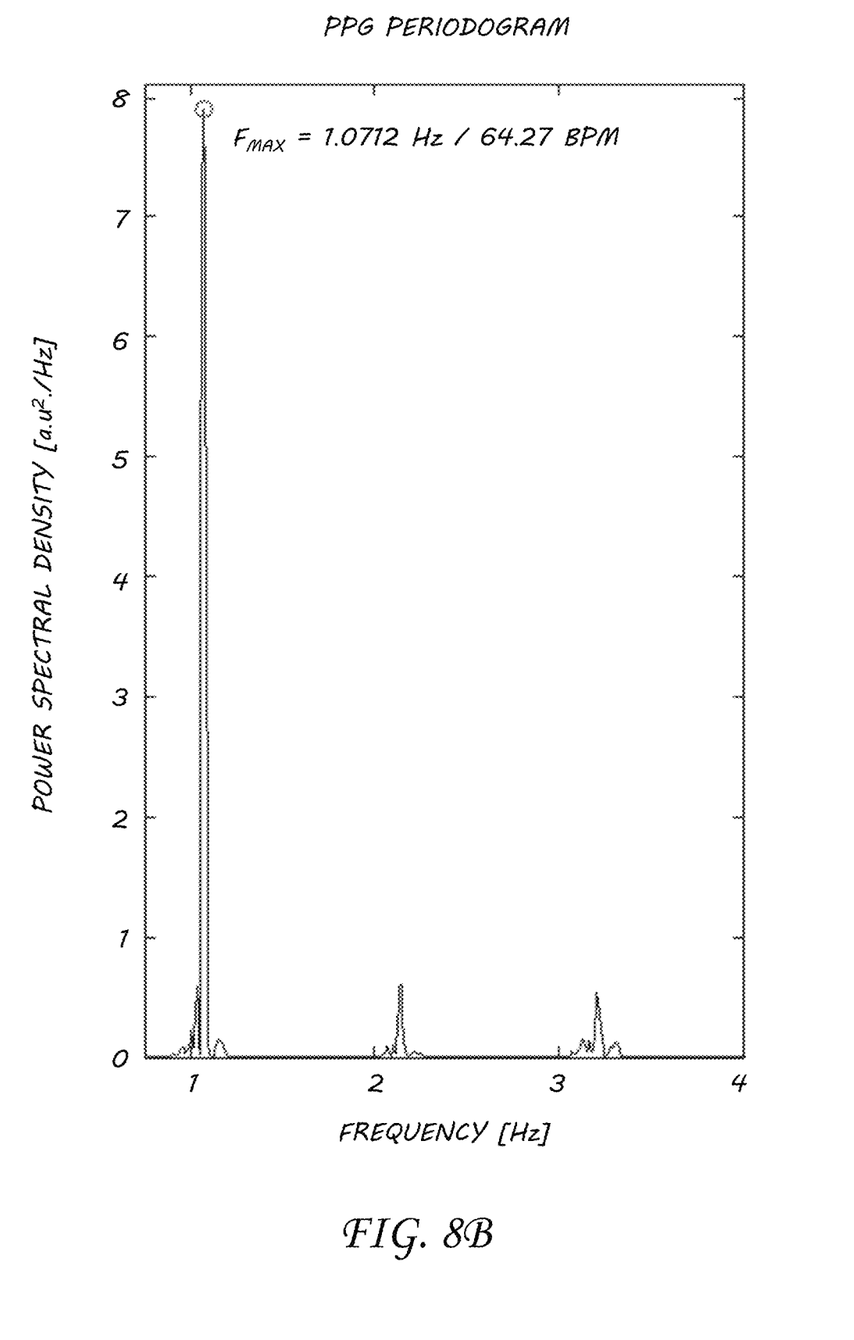

The cardiac information from the PPG component is then extracted in block 52. In this illustrated embodiment, the dominant frequency band power estimate is transformed to relative power by dividing by the component signal power outside the peak frequency range but within 0.75-4 (Hz). The pulse rate component is chosen as the independent component with the highest relative power, as a measure of SNR, and then visually confirmed as the correct component. The resulting component is then segmented into 5, non-overlapping, 1 (min) windows (discarding the 15 (s) pre- and post-buffers). Mean pulse rate for each window was calculated using a periodogram method (with a Hamming window) by finding the frequency with the highest power density in the probable pulse rate range (0.75-4 (Hz) and converting this frequency to [bpm] (60·$f_{max}$). An example of this method for determining pulse rate from the automatically selected ncPPG component is shown in FIG. 8A. As a ground truth comparison, the same method for calculating probable pulse rate was applied to a fingertip PPG data source, shown in FIG. 8B. While power density was used by this illustrated embodiment to extract pulse data, other embodiments may use other extraction methods. The process ends at block 54.

Figure 9:
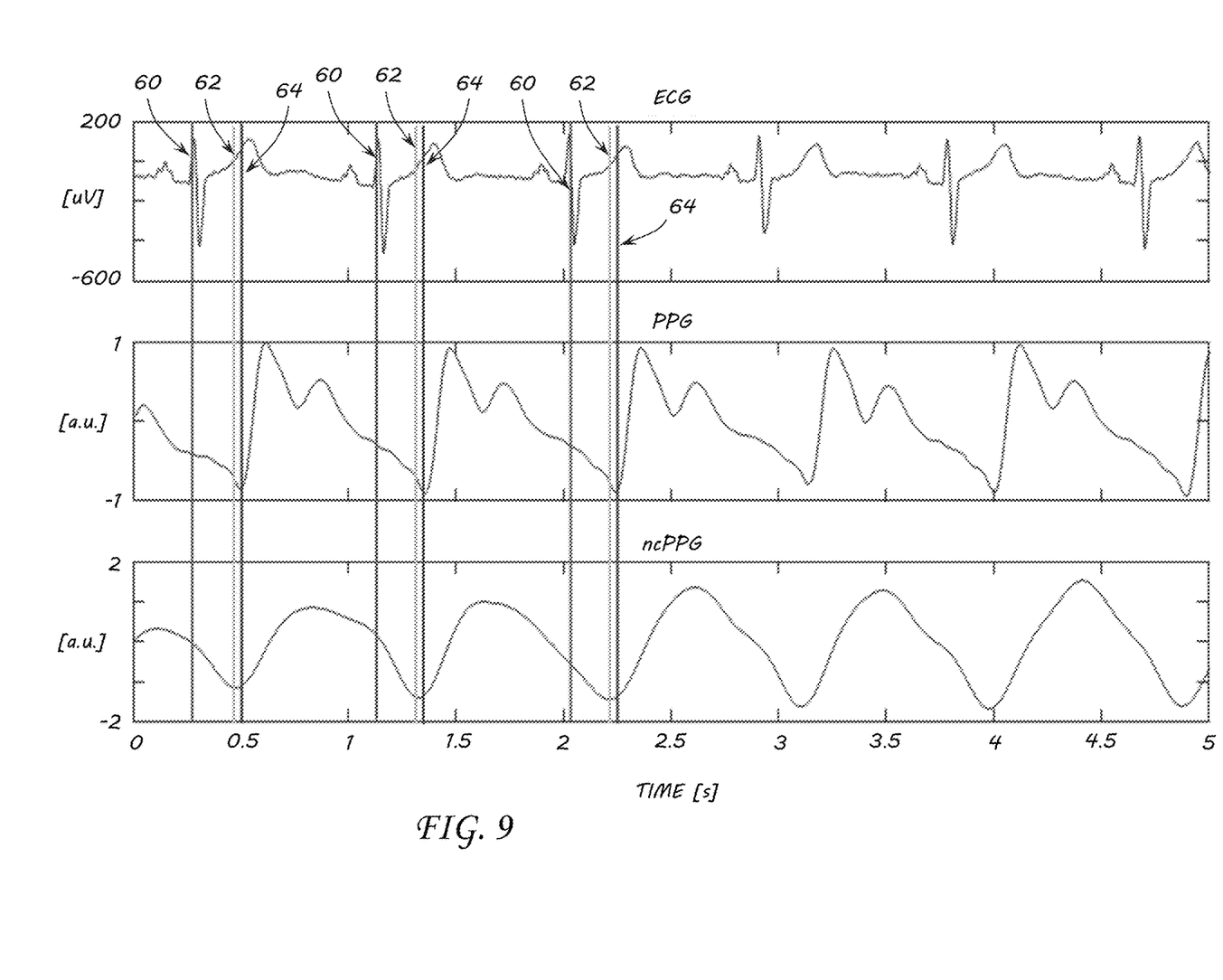
FIG. 9 is a graph containing exemplary time series data from ECG, PPG, and recovered ncPPG components.

An example set of time series data from ECG, PPG, and the recovered ncPPG component is shown in FIG. 9. Indicator lines 60 (Blue), 62 (Green), and 64 (Red) mark the beginning of the systolic phase in the ECG, PPG, and ncPPG time series, respectively. From this data segment, it is clear that the ncPPG source component was accurately recovered from the 9-imager channel space decomposition. Relative timing of systolic onset between ECG, PPG, and ncPPG is consistent with realistic physiological constraints such as pulse wave arrival time being delayed in peripheral vasculature (in the fingertip) as compared to the ncPPG component (facial vasculature).

The results demonstrate the value of a multi-imager acquisition approach for reducing pulse rate recovery error with ncPPG. While the single-imager approach iPPG may be sufficient for situations in which head movement artifact is prevented, even a quasi-stationary participant will produce noticeably larger errors in pulse rate measurement. By contrast, the multi-imager array is successful at reducing pulse rate recovery error to approximately 2 (bpm), even during head motion artifact. This magnitude of error is comparable to the lowest error, under the most favorable conditions, that can be obtained with a single imager and is most promising for the development and transition of ncPPG systems to everyday, natural environments where non-contact cardiopulmonary assessment is either desirable or necessary.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A method for non-contact cardiac assessment of a subject, the method comprising:
    capturing images of the subject from at least two synchronized independent imaging devices spaced equidistant from the subject and positioned such that each imaging device captures an image of the subject different from other imaging devices;
    extracting spectral components of the captured images;
    analyzing the extracted spectral components;
    identifying a signal in the extracted spectral components corresponding to cardiac information; and
    extracting the signal in the extracted spectral components corresponding to the cardiac information,
    wherein identifying a signal in the extracted spectral components corresponding to cardiac information comprises:
        bandpass filtering the extracted spectral components between about 0.3 Hz and about 6 Hz;
        upsampling the extracted spectral components about 1200 Hz using cubic spline interpolation; and
        choosing a signal from the extracted spectral components based on an estimate of signal-to-noise ratio (SNR) in an expected frequency range of a non-contact PPG (ncPPG) component signal.

2. The method of claim 1, wherein capturing the images of the subject from at least two synchronized independent imaging devices comprises:
    capturing images of a head and neck of the subject from the at least two synchronized independent imaging devices.

3. The method of claim 1, wherein extracting spectral components of the captured images comprises:
    extracting Red, Green, and Blue components of the captured images.

4. The method of claim 1, wherein analyzing the extracted spectral components comprises:
    performing an independent component analysis on the extracted spectral components.

5. The method of claim 1, wherein the expected frequency range of an ncPPG component signal is about 0.75 Hz to about 4 Hz.

6. A method for non-contact cardiac assessment of a subject, the method comprising:
    capturing images of the subject from at least two synchronized independent imaging devices spaced equidistant from the subject and positioned such that each imaging device captures an image of the subject different from other imaging devices;
    extracting spectral components of the captured images;
    analyzing the extracted spectral components;
    identifying a signal in the extracted spectral components corresponding to cardiac information; and
    extracting the signal in the extracted spectral components corresponding to the cardiac information,
    wherein extracting the signal in the extracted spectral components corresponding to the cardiac information comprises:
        transforming a band power estimate to relative power by dividing by component signal power outside a peak frequency range but within about 0.75 Hz top about 4 Hz; and
        extracting an independent component with a highest relative power.

7. The method of claim 6, further comprising:
    segmenting the extracted independent component into five non-overlapping windows; and
    finding a frequency with a highest power density in a probable pulse rate range and converting this frequency to beats per minute by 60·$f_{max}$,
    wherein $f_{max}$ is the frequency with the highest power density.

* * * * *